(12) United States Patent
Ito et al.

(10) Patent No.: US 8,795,492 B2
(45) Date of Patent: Aug. 5, 2014

(54) GAS SENSOR ELEMENT

(75) Inventors: Makoto Ito, Nagoya (JP); Fuminori Nakashima, Yokkaichi (JP)

(73) Assignee: Denso Corporation, Kariya (JP)

( * ) Notice: Subject to any disclaimer, the term of this patent is extended or adjusted under 35 U.S.C. 154(b) by 548 days.

(21) Appl. No.: 12/914,298

(22) Filed: Oct. 28, 2010

(65) Prior Publication Data

US 2011/0094883 A1    Apr. 28, 2011

(30) Foreign Application Priority Data

Oct. 28, 2009 (JP) .................................. 2009-248031
Aug. 23, 2010 (JP) .................................. 2010-185940

(51) Int. Cl.
*G01N 27/407* (2006.01)

(52) U.S. Cl.
USPC ............ 204/429; 204/424; 204/428; 204/431

(58) Field of Classification Search
USPC ......... 204/400–402, 404, 409–412, 414–433; 205/775, 775.5, 780.5, 781, 782–787, 205/794.5; 73/23.31, 23.32; 60/274–276, 60/282
See application file for complete search history.

(56) References Cited

U.S. PATENT DOCUMENTS

| | | | |
|---|---|---|---|
| 4,297,192 A * | 10/1981 | Shinohara et al. ............ | 204/428 |
| 5,800,689 A | 9/1998 | Hori et al. | |
| 2002/0070110 A1 * | 6/2002 | Naito ............................ | 204/426 |
| 2003/0159928 A1 | 8/2003 | Kojima et al. | |
| 2007/0144905 A1 * | 6/2007 | Tsuji et al. ..................... | 204/424 |
| 2007/0151851 A1 | 7/2007 | Tanaka et al. | |
| 2010/0147685 A1 * | 6/2010 | Ikawa et al. ................... | 204/431 |
| 2010/0155240 A1 * | 6/2010 | Matsuoka et al. ............. | 204/424 |

FOREIGN PATENT DOCUMENTS

| | | |
|---|---|---|
| EP | 1742043 A1 * | 1/2007 |
| JP | 08-240559 | 9/1996 |
| JP | 10-170474 | 6/1998 |
| JP | 2006-171013 | 6/2006 |
| JP | 2007-206055 | 8/2007 |
| JP | 2007-218894 | 8/2007 |
| JP | 2008-216241 | 9/2008 |
| JP | 2009-080111 | 4/2009 |

OTHER PUBLICATIONS

Tetsuya JP2009080111A Apr. 2009, machine translation.*
Japanese Office Action issued for Japanese Patent No. 2010-185940, dated Feb. 5, 2013 (with English Translation).

* cited by examiner

*Primary Examiner* — Susan D Leong
(74) *Attorney, Agent, or Firm* — Nixon & Vanderhye P.C.

(57) ABSTRACT

A gas sensor element includes a solid electrolyte body having oxygen ion conductivity, a pair of measurement and reference electrodes respectively provided on an opposite pair of first and second surfaces of the solid electrolyte body, a porous diffusion-resistant layer through which a measurement gas is introduced to the measurement electrode, and a protective layer. The protective layer is provided to cover, at least, an outer surface of the porous diffusion-resistant layer through which the measurement gas flows into the diffusion-resistant layer. The protective layer is hydrophilic at room temperature and water-repellent at high temperatures at which the solid electrolyte body can be activated.

7 Claims, 10 Drawing Sheets

FIG.13

| SAMPLE | MATERIAL | SURFACE ROUGHNESS Ra (μm) | THICKNESS (μm) | WATER-INDUCED CRACKING | ACTIVATION TIME | RESPON-SIVENESS | DURABILITY |
|---|---|---|---|---|---|---|---|
| E1 | α-ALUMINA | 0.7 | 30 | ○ | ○ | ○ | ○ |
| E2 | α-ALUMINA | 1.2 | 30 | ○ | ○ | ○ | ○ |
| E3 | α-ALUMINA | 1.5 | 30 | ○ | ○ | ○ | ○ |
| E4 | α-ALUMINA | 2.0 | 30 | ○ | ○ | ○ | ○ |
| E5 | α-ALUMINA | 2.7 | 30 | ○ | ○ | ○ | ○ |
| E6 | α-ALUMINA | 3.0 | 30 | ○ | ○ | ○ | ○ |
| E7 | α-ALUMINA | 2.0 | 70 | ○ | ○ | ○ | ○ |
| E8 | α-ALUMINA | 2.0 | 100 | ○ | ○ | ○ | ○ |
| E9 | α-ALUMINA | 2.0 | 150 | ○ | ○ | ○ | ○ |
| E10 | TITANIA | 2.3 | 70 | ○ | ○ | ○ | ○ |
| E11 | ZIRCONIA | 2.3 | 70 | ○ | ○ | ○ | ○ |
| E12 | SILICON CARBIDE | 2.1 | 70 | ○ | ○ | ○ | ○ |
| E13 | SILICON NITRIDE | 2.2 | 70 | ○ | ○ | ○ | ○ |
| E14 | ZINC OXIDE | 2.3 | 70 | ○ | ○ | ○ | ○ |
| C1 | α-ALUMINA | 2.5 | 210 | ○ | × | × | ○ |
| C2 | α-ALUMINA | 3.5 | 100 | × | ○ | ○ | ○ |
| C3 | CaF2 | 1.8 | 50 | ○ | × | ○ | ○ |
| C4 | BN | 2.0 | 75 | ○ | × | ○ | ○ |

GAS SENSOR ELEMENT

CROSS-REFERENCES TO RELATED APPLICATIONS

This application is based on and claims priority from Japanese Patent Applications No. 2009-248031 filed on Oct. 28, 2009 and No. 2010-185940 filed on Aug. 23, 2010, the contents of which are hereby incorporated by reference in their entireties into this application.

BACKGROUND OF THE INVENTION

1. Technical Field of the Invention

The present invention relates to a gas sensor element for sensing the concentration of a specific component in a gas to be measured (to be simply referred to as a measurement gas hereinafter).

2. Description of the Related Art

In the exhaust system of an internal combustion engine of a motor vehicle, there is generally arranged a gas sensor for sensing the concentration of a specific component (e.g., the concentration of oxygen) in the exhaust gas from the engine.

The gas sensor has, for example, a known gas sensor element built therein. The known gas sensor element includes: a solid electrolyte body having oxygen ion conductivity and an opposite pair of first and second surfaces; a measurement electrode provided on the first surface of the solid electrolyte body so as to be exposed to the measurement gas (i.e., the exhaust gas from the engine); a reference electrode provided on the second surface of the solid electrolyte body so as to be exposed to a reference gas (e.g., air); and a porous diffusion-resistant layer through which the measurement gas is introduced to the measurement electrode.

However, the known gas sensor element involves the following problem.

The gas sensor element has an outer surface to be exposed the flow of the exhaust gas from the engine. During startup of the engine, steam contained in the exhaust gas will condense into water droplets, and the water droplets will flow along with the exhaust gas toward the gas sensor element. The gas sensor element is generally used at high temperatures (e.g., not lower than 500° C.) at which the solid electrolyte body can be activated. Therefore, upon adherence of the water droplets to the outer surface of the gas sensor element, a large thermal shock may occur in the gas sensor element, thereby inducing cracking of the gas sensor element (to be referred to as water-induced cracking hereinafter).

To solve the above problem, Japanese Patent Application Publication No. 2006-171013 discloses a first technique, according to which a porous protective layer is provided at the outer periphery of the gas sensor element. Consequently, water droplets, which have adhered to the gas sensor element, can be dispersed into the porous protective layer, thereby preventing water-induced cracking of the gas sensor element.

However, with the first technique, to reliably prevent water-induced cracking of the gas sensor element, it is necessary to set the thickness of the porous protective layer sufficiently large. As a result, the heat capacity of the entire gas sensor element will be accordingly increased, thereby making it difficult to ensure both prompt activation and high responsiveness of the gas sensor element.

Japanese Patent Application Publication No. H8-240559 discloses a second technique, according to which a water-repellent surface layer is provided at the outer periphery of the gas sensor element. Consequently, water droplets, which approach the gas sensor element, can be repelled by the surface layer, thereby preventing water-induced cracking of the gas sensor element.

However, with the second technique, the surface layer is always water-repellent even at room temperature. Consequently, it may be difficult to accurately conduct a super-insulation inspection for the gas sensor element before use.

More specifically, the super-insulation inspection is generally conducted at room temperature by (1) immersing the gas sensor element in water or a liquid mixture of water and alcohol for a given time, thereby making water or the liquid mixture permeate into microcracks of the gas sensor element; (2) applying a predetermined voltage across the measurement and reference electrodes of the gas sensor element; and (3) measuring the electrical resistance between the two electrodes. However, since the surface layer of the gas sensor element is water-repellent at room temperature, it may be difficult to make water or the liquid mixture of water and alcohol sufficiently permeate into the microcracks of the gas sensor element. Consequently, it may be difficult to accurately conduct the super-insulation inspection for the gas sensor element.

Moreover, with the second technique, the surface layer is made of at least one of hydrophobic materials which include BN, $CaF_2$, NbC, $ZrB_2$, $TiB_2$, and talc. However, it is easy for those hydrophobic materials to be oxidized at high temperatures. Consequently, in a lean atmosphere (i.e., an atmosphere containing a greater amount of oxygen), it may be difficult to accurately sense the concentration of the specific component in the measurement gas in an early stage, thus resulting in an increase in the activation time of the gas sensor element (i.e., the length of time from when the activation of the gas sensor element is started to when the gas sensor element becomes able to accurately sense the concentration of the specific component in the measurement gas). As a result, it may be difficult to ensure prompt activation of the gas sensor element.

SUMMARY OF THE INVENTION

According to the present invention, there is provided a gas sensor element which includes a solid electrolyte body, a measurement electrode, a reference electrode, a porous diffusion-resistant layer, and a protective layer. The solid electrolyte body has oxygen ion conductivity and an opposite pair of first and second surfaces. The measurement electrode is provided on the first surface of the solid electrolyte body so as to be exposed to a measurement gas. The reference electrode is provided on the second surface of the solid electrolyte body so as to be exposed to a reference gas. The porous diffusion-resistant layer is provided so that through it, the measurement gas is introduced to the measurement electrode. The porous diffusion-resistant layer has an outer surface through which the measurement gas flows into the diffusion-resistant layer. The protective layer is provided to cover at least the outer surface of the porous diffusion-resistant layer. The protective layer is hydrophilic at room temperature and water-repellent at high temperatures at which the solid electrolyte body can be activated.

With the above configuration, since the protective layer is hydrophilic at room temperature, it is possible to allow, in conducting a super-insulation inspection for the gas sensor element, water or a liquid mixture of water and alcohol to sufficiently permeate into microcracks of the gas sensor element. Consequently, it is possible accurately conduct the super-insulation inspection for the gas sensor element.

Moreover, the protective layer is water-repellent at high temperatures at which the solid electrolyte body can be activated. In other words, the protective layer is water-repellent during operation of the gas sensor element. Therefore, when water droplets approach the protective layer, the water droplets will be instantly repelled by the protective layer. Consequently, it is possible to suppress the decrease in the temperature of the gas sensor element due to the water droplets, thereby preventing large thermal shock from occurring in the gas sensor element. As a result, it is possible to prevent water-induced cracking of the gas sensor element.

In particular, since the diffusion-resistant layer is a porous layer, during operation of the gas sensor element, it is generally easy for water droplets to disperse into the diffusion-resistant layer, causing a large thermal shock to occur in the diffusion-resistant layer. However, according to the present invention, there is provided the protective layer to cover at least the outer surface of the porous diffusion-resistant layer. Consequently, with the protective layer, it is possible to block water droplets from dispersing into the porous diffusion-resistant layer, thereby preventing thermal shock from occurring in the diffusion-resistant layer.

In addition, since the protective layer is water-repellent at high temperatures, it is unnecessary to set the thickness of the protective layer large for the purpose of preventing water-induced cracking of the gas sensor element. In other words, it is possible to set the thickness of the protective layer small. Consequently, it is possible to suppress the heat capacity of the gas sensor element, thereby ensuring prompt activation of the gas sensor element.

The gas sensor element according to the invention may be used in an A/F (Air/Fuel) ratio sensor that is disposed in the exhaust system of an internal combustion engine of a motor vehicle to sense the A/F ratio of air-fuel mixture supplied to the engine. More specifically, in this case, the A/F ratio sensor may determine the A/F ratio based on the limit current of the gas sensor element which depends on the concentration of oxygen in the exhaust gas from the engine. Otherwise, the gas sensor element may be used in an oxygen sensor that is disposed in the exhaust system of an internal combustion engine of a motor vehicle to sense the concentration of oxygen in the exhaust gas from the engine.

As described above, the gas sensor element according to the invention includes the protective layer that is hydrophilic at room temperature and water-repellent at high temperatures at which the solid electrolyte body can be activated. Here, "room temperature" is generally within 20±15° C. (i.e., 5-35° C.); "high temperatures at which the solid electrolyte body can be activated" means "temperatures higher than the activation temperature of the solid electrolyte body". In addition, "high temperatures at which the solid electrolyte body can be activated" may be, for example, higher than or equal to 500° C., and is higher than or equal to 700° C. in the first embodiment of the invention which is to be described later.

The water-repellency of the protective layer at high temperatures can be obtained by, for example, causing the Leidenfrost effect at the protective layer. More specifically, when the Leidenfrost effect is caused at the protective layer, water droplets, which approach the protective layer, will produce a heat-insulating vapor layer between the protective layer and the water droplets. The heat-insulating vapor layer will cause the water droplets to instantly leave the protective layer without being further heated by the high temperature of the protective layer.

It is preferable that the protective layer has a surface roughness Ra lower than or equal to 3.0 µm. In this case, when water droplets approach the protective layer at high temperatures, it is possible to reliably cause the Leidenfrost effect at the protective layer, thereby rendering the protective layer water-repellent.

Moreover, the surface roughness Ra of the protective layer has a correlation with the average particle diameter of particles that form the protective layer. Therefore, in terms of suitably setting the average particle diameter to ensure high responsiveness of the gas sensor element, it is preferable for the surface roughness Ra to be higher than or equal to 0.6 µm.

In addition, it should be noted that the surface roughness Ra of the protective layer is an arithmetic means roughness according to JIS B 0601:2001 (or ISO 4287:1997).

It is preferable that the protective layer is made of a ceramic comprising at least one of α-alumina, titania, zirconia, silicon carbide, silicon nitride, and zinc oxide. In this case, since all of the above materials are hydrophilic, it is possible to reliably render the protective layer hydrophilic at room temperature. Moreover, since all of the above materials are hardly oxidized at high temperatures, in a lean atmosphere (i.e., an atmosphere containing a greater amount of oxygen), it is possible to accurately sense the concentration of a specific component in the measurement gas in an early stage. Consequently, it is possible to prevent the activation time of the gas sensor element (i.e., the length of time from when the activation of the gas sensor element is started to when the gas sensor element becomes able to accurately sense the concentration of the specific component in the measurement gas) from being increased due to oxidization of the above materials, thereby ensuring prompt activation of the gas sensor element.

It is also preferable that the protective layer has a thickness in the range of 20 to 150 µm. In this case, it is possible to ensure both prompt activation and high responsiveness of the gas sensor element 1.

In addition, if the thickness of the protective layer is less than 20 µm, it may be difficult to set the surface roughness Ra of the protective layer to be lower than or equal to 3.0 µm due to the influence of a layer (e.g., the porous diffusion-resistant layer) underlying the protective layer. On the other hand, if the thickness of the protective layer is greater than 150 µm, it may be difficult to ensure both prompt activation and high response of the gas sensor element.

It is preferable that the protective layer has a porosity in the range of 10 to 50%. In this case, it is possible to ensure sufficient gas-permeability of the protective layer and thereby ensure high responsiveness of the gas sensor element while ensuring high strength of the protective layer.

In addition, if the porosity of the protective layer is less than 10%, it may be difficult to ensure sufficient gas-permeability of the protective layer and thus difficult to ensure high responsiveness of the gas sensor element. On the other hand, if the porosity of the protective layer is less than 50%, it may be difficult to ensure high strength of the protective layer.

It is preferable that the protective layer is formed over the entire outer periphery of the gas sensor element. In this case, it is possible to more reliably prevent water-induced cracking of the gas sensor element.

It is further preferable that a portion of the protective layer, which does not cover the outer surface of the porous diffusion-resistant layer, has a thickness less than or equal to 10 µm. In this case, it is possible to suppress the heat capacity and thereby ensure prompt activation of the gas sensor element while reliably preventing water-induced cracking of the gas sensor element.

Moreover, in terms of reliably preventing water-induced cracking of the gas sensor element over, it is also preferable for the thickness of the portion of the protective layer to be greater than or equal to 5 µm.

It is preferable that the gas sensor element further includes a trap layer that is interposed between the outer surface of the porous diffusion-resistant layer and the protective layer to trap poisoning substances contained in the measurement gas. In this case, it is possible to prevent the porous diffusion-resistant layer from being clogged and the measurement electrode from being poisoned by the poisoning substances contained in the measurement gas, thereby ensuring high accuracy, high responsiveness, and stable output of the gas sensor element.

It is further preferable that the trap layer completely covers the outer surface of the porous diffusion-resistant layer. In this case, it is possible for the trap layer to reliably trap the poisoning substances contained in the measurement gas.

Moreover, it is also possible to form the trap layer to cover, in addition to the outer surface of the porous diffusion-resistant layer, other portions of the gas sensor element.

In addition, the trap layer may include porous particles having a large specific surface which are made of at least one of γ-alumina, θ-alumina, and magnesia.

It is further preferable that the trap layer is able to trap chemical compounds produced from the components of an engine oil which include P, Si, Ca, and Zn.

BRIEF DESCRIPTION OF THE DRAWINGS

The present invention will be understood more fully from the detailed description given hereinafter and from the accompanying drawings of preferred embodiments of the invention, which, however, should not be taken to limit the invention to the specific embodiments but are for the purpose of explanation and understanding only.

In the accompanying drawings:

FIG. 13 is a tabular representation showing the results of Experiment 3 of the invention.

DESCRIPTION OF PREFERRED EMBODIMENTS

Figure 1:
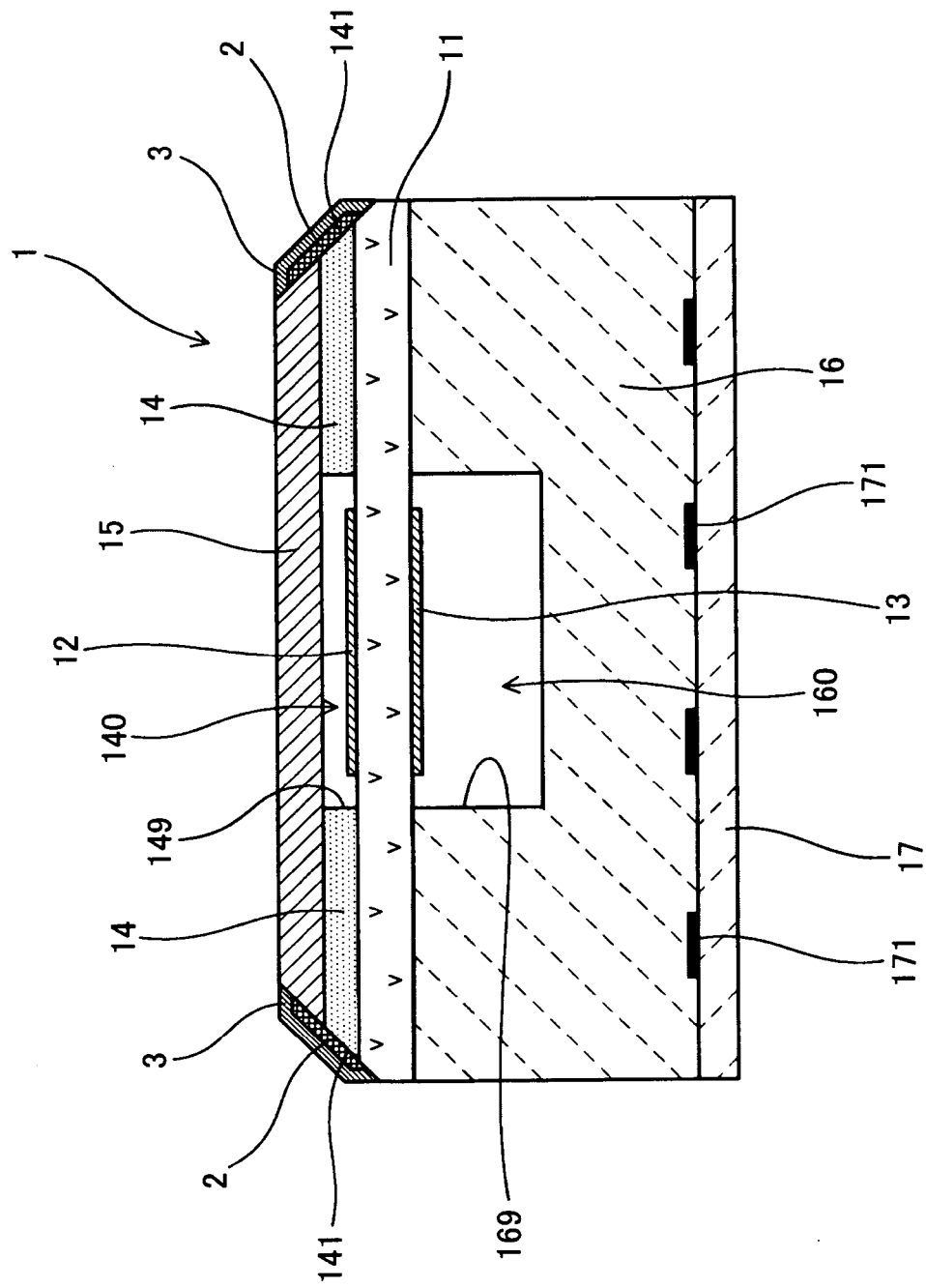
FIG. 1 is a cross-sectional view of a gas sensor element according to the first embodiment of the invention.

Preferred embodiments of the present invention will be described hereinafter with reference to FIGS. 1-13. It should be noted that for the sake of clarity and understanding, identical components having identical functions in different embodiments of the invention have been marked, where possible, with the same reference numerals in each of the figures and that for the sake of avoiding redundancy, descriptions of the identical components will not be repeated.

First Embodiment

FIG. 1 shows the overall configuration of a gas sensor element 1 according to the first embodiment of the invention. In the present embodiment, the gas sensor element 1 is configured to be used in an A/F (Air/Fuel) ratio sensor that is disposed in the exhaust system of an internal combustion engine of a motor vehicle to sense the A/F ratio of air-fuel mixture supplied to the engine. More specifically, the A/F sensor determines the A/F ratio based on the limit current flowing between electrodes of the gas sensor element 1; the limit current depends on the concentration of oxygen in the exhaust gas from the engine.

As shown in FIG. 1, the gas sensor element 1 includes a solid electrolyte body 11, a measurement electrode 12, a reference electrode 13, and a porous diffusion-resistant layer 14. The solid electrolyte body 11 has oxygen ion conductivity and an opposite pair of first and second surfaces (i.e., the upper and lower surfaces in FIG. 1). The measurement electrode 12 is provided on the first surface of the solid electrolyte body 11 so as to be exposed to a measurement gas (i.e., the exhaust gas from the engine in the present embodiment). The reference electrode 13 is provided on the second surface of the solid electrolyte body 11 so as to be exposed to a reference gas (i.e., air in the present embodiment). The porous diffusion-resistant layer 14 is provided on the first surface of the solid electrolyte body 11 around the measurement electrode 12, so that the measurement gas is introduced to the measurement electrode 12 through the porous diffusion-resistant layer 14.

Figure 2:
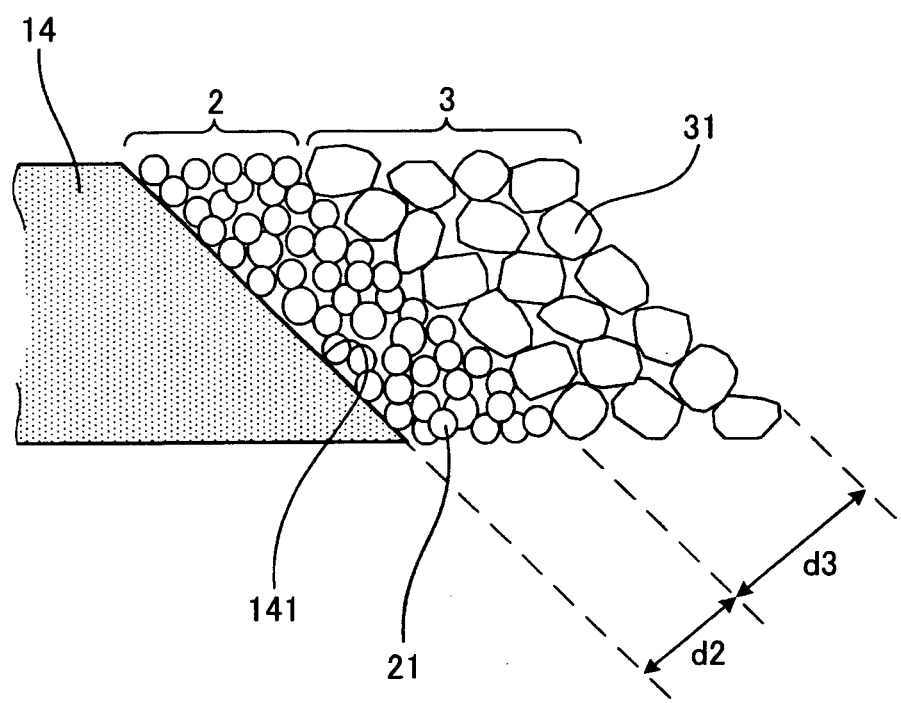
FIG. 2 is a schematic view illustrating the formation of a trap layer and a protective layer on an outer side surface of a porous diffusion-resistant layer in the gas sensor element according to the first embodiment.

Referring now to FIG. 2 together with FIG. 1, the gas sensor element 1 further includes a trap layer 2 and a protective layer 3. The trap layer 2 is formed on an outer side surface 141 of the porous diffusion-resistant layer 14, through which the measurement gas flows into the layer 14, to trap (or collect) poisoning substances contained in the measurement gas. The protective layer 3 is formed on the trap layer 2. The protective layer 3 is hydrophilic at room temperature and water-repellent at high temperatures at which the solid electrolyte body 11 can be activated.

Hereinafter, the configuration of the gas sensor element 1 according to the present embodiment will be described in detail.

As shown in FIG. 1, in the gas sensor element 1, the measurement and reference electrodes 12 and 13 are respectively provided on the first and second surfaces of the solid electrolyte body 11 that has oxygen ion conductivity. The solid electrolyte body 11 is made of, for example, zirconia. Both the measurement and reference electrodes 12 and 13 are made of, for example, platinum (Pt).

The porous diffusion-resistant layer 14 is made of, for example, gas-permeable porous alumina. The diffusion-resistant layer 14 has an opening portion 149 that faces the measurement electrode 12.

The gas sensor element 1 further includes a shield layer 15, a reference gas chamber formation layer 16, and a heater substrate 17. The gas sensor element 1 also has both a measurement gas chamber 140 and a reference gas chamber 160 formed therein.

The shield layer 15 is provided on the surface of the porous diffusion-resistant layer 14 on the opposite side to the solenoid electrolyte body 11. The shield layer 15 is made of, for example, dense alumina that is gas impermeable and electrically insulative.

Between the solid electrolyte body 11, the opening portion 149 of the porous diffusion-resistant layer 14, and the shield layer 15, there is formed a hollow space which makes up the measurement gas chamber 140. During operation of the gas sensor element 1, the measurement gas chamber 140 will be filled with the measurement gas which is introduced thereinto via the porous diffusion-resistant layer 14; thus, the measurement electrode 12 will, be accordingly exposed to the measurement gas.

The reference gas chamber formation layer 16 is provided on the second surface (i.e., the lower surface in FIG. 1) of the solid electrolyte body 11. The reference gas chamber formation layer 16 is made of, for example, dense alumina that is gas impermeable and electrically insulative. In the reference gas chamber formation layer 16, there is formed a recess 169 for making up the reference gas chamber 160. During operation of the gas sensor element 1, the reference gas chamber 160 will be filled with the reference gas which is introduced thereinto via an opening (not shown) of the chamber 160; thus, the reference electrode 13 will be accordingly exposed to the reference gas.

The heater substrate 17 is provided on the surface of the reference gas chamber formation layer 16 on the opposite side to the solid electrolyte body 11. A plurality of electrical heating elements 171 are provided in the heater substrate 17 so as to face the reference gas chamber formation layer 16. During startup of the engine, the heating elements 171 will be supplied with electric power to generate heat, thereby heating the gas sensor element 1 to its activation temperature.

The trap layer 2 is formed on the outer side surface 141 of the porous diffusion-resistant layer 14, through which the measurement gas flows into the diffusion-resistant layer 14. In other words, the trap layer 2 is interposed between the outer side surface 141 of the porous diffusion-resistant layer 14 and the protective layer 3.

The trap layer 2 is a porous layer comprised of ceramic particles 21 that are made mostly of γ-alumina. The trap layer 2 is configured to trap poisoning substances contained in the measurement gas, such as chemical compounds produced from the components of an engine oil which include P, Si, Ca, and Zn. The trap layer 2 has a thickness d2 of 100 μm and a porosity of 40%.

The protective layer 3 is formed on the outer surface of the trap layer 2. In other words, the protective layer 3 is provided to cover the outer side surface 141 of the porous diffusion-resistant layer 14 with the trap layer 2 interposed between the protective layer 3 and the outer side surface 141. The protective layer 3 is hydrophilic at room temperature which is generally in the range of 5 to 35° C. However, at temperatures higher than or equal to 700° C., in other words during operation of the gas sensor element 1, the protective layer 3 is water-repellent. The protective layer 3 is a dense layer comprised of ceramic particles 31 that are made mostly of α-alumina. The protective layer 3 has a surface roughness Ra of 1.5 μm, a thickness d3 of 30 μm, and a porosity of 50%.

Figure 3:
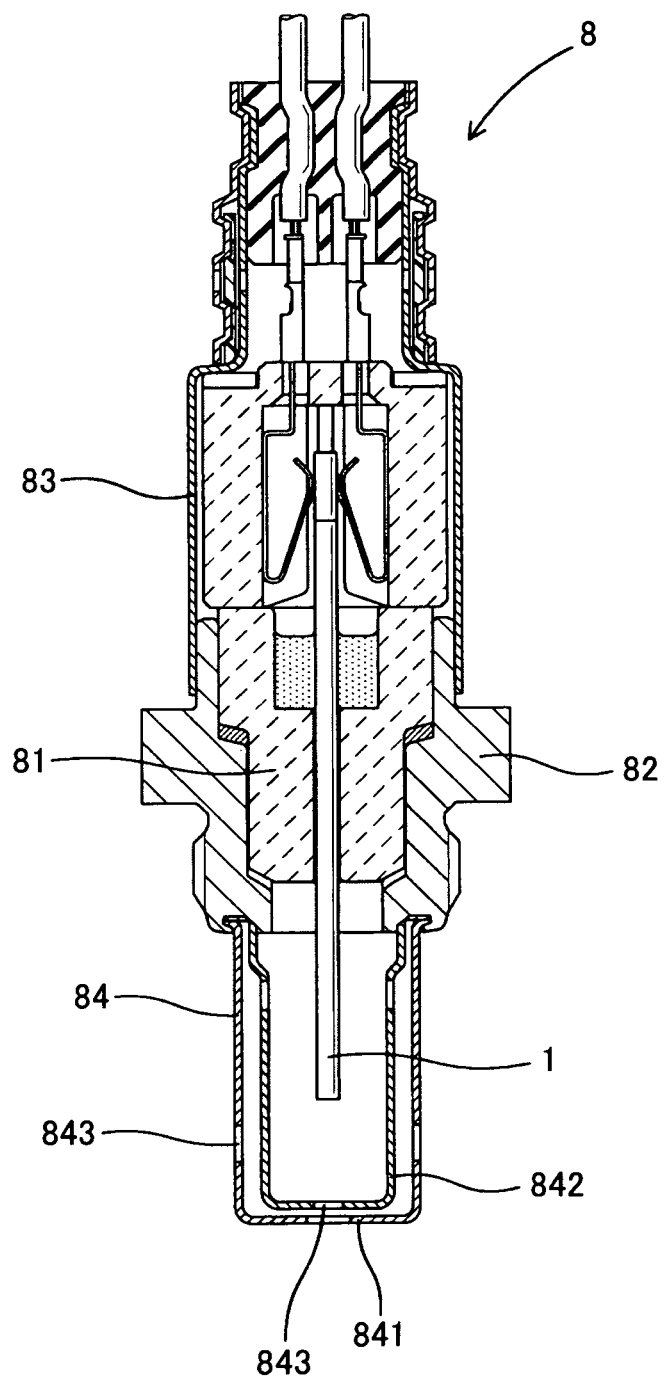
FIG. 3 is a cross-sectional view of a gas sensor that includes the gas sensor element according to the first embodiment.

Next, a gas sensor 8 which has the gas sensor element 1 incorporated therein will be described with reference to FIG. 3.

The gas sensor 8 includes, in addition to the gas sensor element 1, an insulator 81, a housing 82, a base-side cover 83, and a tip-side cover 84. The insulator 81 has the gas sensor element 1 partially inserted and held therein. The housing 82 has the insulator 81 partially inserted and held therein. The base-side cover 83 is fixed to a base end (i.e., the upper end in FIG. 3) of the housing 82 to protect that part of the insulator 81 which protrudes from the base end of the housing 81. The tip-side cover 84 is fixed to a tip end (i.e., the lower end in FIG. 3) of the housing 82 to protect that part of the gas sensor element 1 which protrudes from the tip end of the housing 82. The tip-side cover 84 is a double cover consisting of an outer cover 841 and an inner cover 842. Each of the inner and outer covers 841 and 842 has through-holes 843 formed through its end and side walls. During operation of the gas sensor 8, the measurement gas will be introduced to the gas sensor element 1 through the through-holes 843 of the inner and outer covers 841 and 842.

The above-described gas sensor element 1 according to the present embodiment has the following advantages.

In the present embodiment, the gas sensor element 1 includes the protective layer 3 that is provided to cover the outer side surface 141 of the porous diffusion-resistant layer 14.

The protective layer 3 is hydrophilic at room temperature. Therefore, in conducting a super-insulation inspection for the gas sensor element 1, it is possible to allow water or a liquid mixture of water and alcohol to sufficiently permeate into microcracks of the gas sensor element 1. As a result, it is possible accurately conduct the super-insulation inspection for the gas sensor element 1.

Moreover, the protective layer 3 is water-repellent at high temperatures at which the solid electrolyte body 11 can be activated. In other words, the protective layer 3 is water-repellent during operation of the gas sensor element 1. Therefore, when water droplets approach the protective layer 3, the water droplets will be instantly repelled by the protective layer 3. Consequently, it is possible to suppress the decrease in the temperature of the gas sensor element 1 due to the water droplets, thereby preventing a large thermal shock from occurring in the gas sensor element 1. As a result, it is possible to prevent water-induced cracking of the gas sensor element 1.

In particular, since the diffusion-resistant layer 14 is a porous layer, during operation of the gas sensor element 1, it is generally easy for water droplets to disperse into the diffusion-resistant layer 14, thereby causing a large thermal shock to occur in the diffusion-resistant layer 14. However, in the present embodiment, there is provided the protective layer 3 to cover the outer side surface 141 through which the measurement gas flows into the porous diffusion-resistant layer 14. Consequently, with the protective layer 3, it is possible to block water droplets from dispersing into the diffusion-resistant layer 14, thereby preventing thermal shock from occurring in the diffusion-resistant layer 14.

In addition, since the protective layer 3 is water-repellent at high temperatures, it is unnecessary to set the thickness d3 of the protective layer 3 large for the purpose of preventing water-induced cracking of the gas sensor element 1. In other words, it is possible to set the thickness d3 of the protective layer 3 small. Consequently, it is possible to suppress the heat capacity of the gas sensor element 1, thereby ensuring prompt activation of the gas sensor element 1.

In the present embodiment, the protective layer 3 has a surface roughness Ra lower than or equal to 3.0 μm. Consequently, when water droplets approach the protective layer 3 at high temperatures, it is possible to reliably cause the Leidenfrost effect at the protective layer 3, thereby rendering the protective layer 3 water-repellent.

In the present embodiment, the thickness d3 of the protective layer 3 is set to be in the range of 20 to 150 μm. Consequently, it is possible to ensure both prompt activation and high responsiveness of the gas sensor element 1.

In the present embodiment, the protective layer 3 has a porosity in the range of 10 to 50%. Consequently, it is possible to ensure sufficient gas-permeability of the protective layer 3 and thus high responsiveness of the gas sensor element 1 while ensuring high strength of the protective layer 3.

In the present embodiment, the protective layer 3 is made of a ceramic that is composed mostly of α-alumina. Since α-alumina is hydrophilic, it is possible to reliably render the protective layer 3 hydrophilic at room temperature. Moreover, since α-alumina is hardly oxidized at high temperatures, it is possible to accurately sense the concentration of oxygen (i.e., a specific component) in the exhaust gas (i.e., the measurement gas) in an early stage. Consequently, it is possible to prevent the activation time of the gas sensor element 1 (i.e., the length of time from when the activation of the gas sensor element 1 is started to when the gas sensor element 1 becomes able to accurately sense the concentration of oxygen in the exhaust gas) from being increased due to oxidization of the ceramic forming the protective layer 3, thereby ensuring prompt activation of the gas sensor element 1.

It should be noted that the ceramic fox wing the protective layer 3 may also include titania, zirconia, silicon carbide, silicon nitride, and zinc oxide.

In the present embodiment, the gas sensor element 1 includes the trap layer 2 that is interposed between the outer side surface 141 of the porous diffusion-resistant layer 14 and the protective layer 3 to trap poisoning substances contained in the measurement gas. Consequently, it is possible to prevent the porous diffusion-resistant layer 14 from being clogged and the measurement electrode 13 from being poisoned by the poisoning substances contained in the measurement gas, thereby ensuring high accuracy, high responsiveness, and stable output of the gas sensor element 1.

[Modification 1]

In the previous embodiment, as shown FIG. 1 both the trap layer 2 and the protective layer 3 are formed only to cover the outer side surface 141 of the porous diffusion-resistant layer 14.

Figure 4:
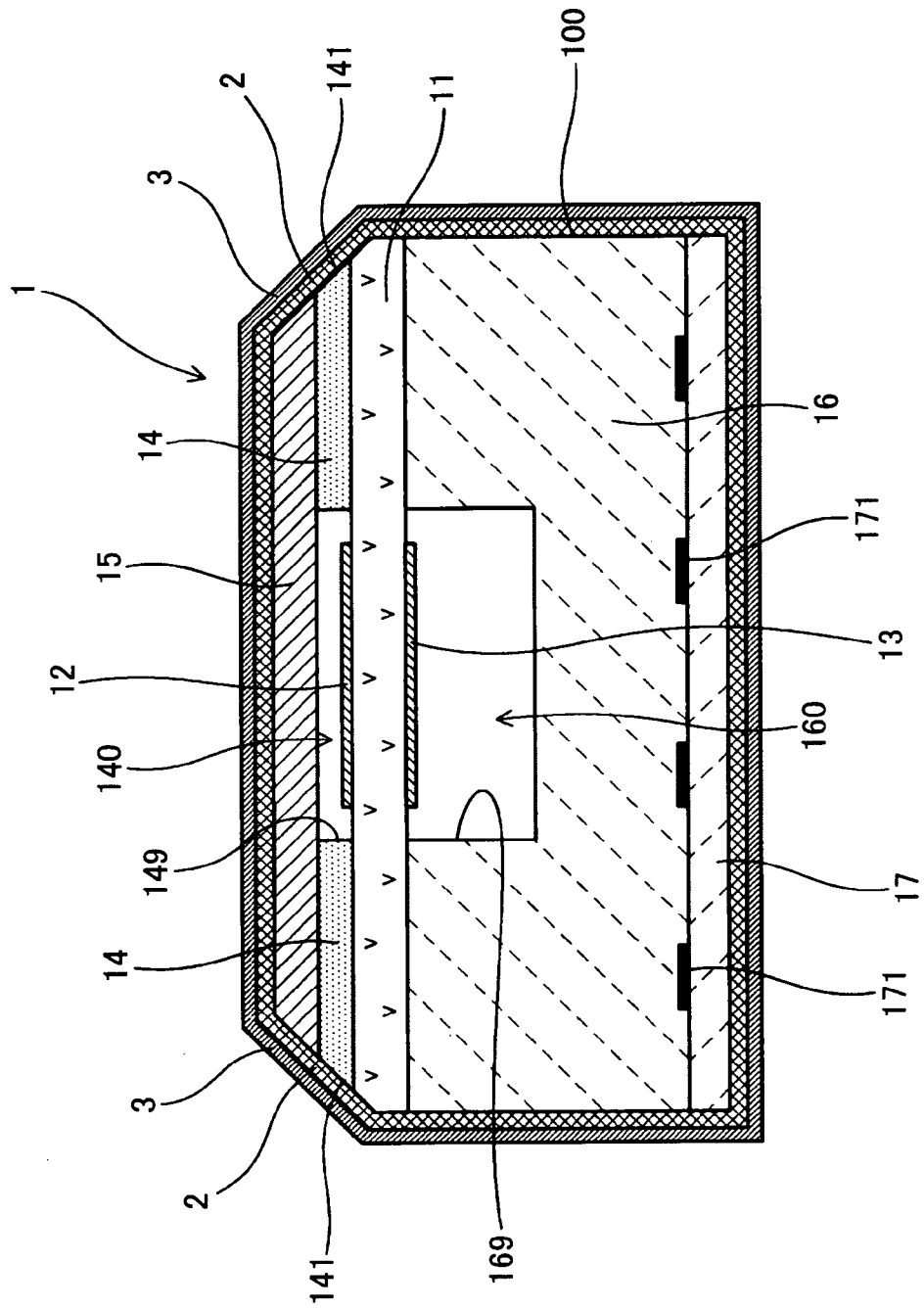
FIG. 4 is a cross-sectional view of a gas sensor element according to a modification of the first embodiment.

However, as shown in FIG. 4, it is also possible to form both the trap layer 2 and the protective layer 3 to extend over the entire outer periphery 100 of the gas sensor element 1.

In addition, though not graphically shown, it is also possible to form only one of the trap layer 2 and the protective layer 3 to extend over the entire outer periphery 100 of the gas sensor element 1 while forming the other only to cover the outer side surface 141 of the porous diffusion-resistant layer 14.

[Modification 2]

In the previous embodiment, as shown in FIG. 1, there is interposed the trap layer 2 between the outer side surface 141 of the porous diffusion-resistant layer 14 and the protective layer 3.

Figure 5:
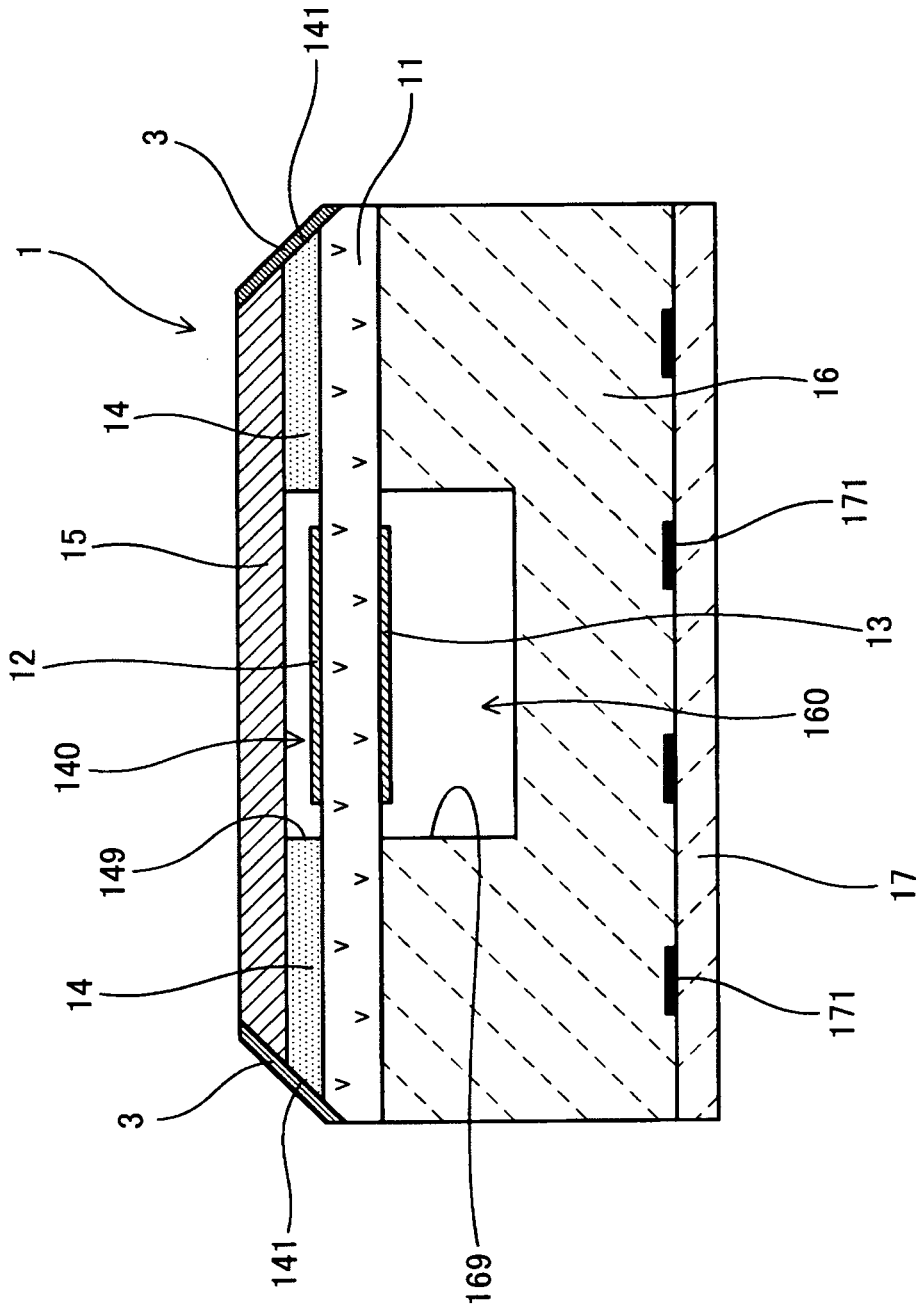
FIG. 5 is a cross-sectional view of a gas sensor element according to another modification of the first embodiment.

However, as shown in FIG. 5, it is also possible to omit the trap layer 2 from the gas sensor element 1, forming the protective layer 3 directly on the outer side surface 141 of the porous diffusion-resistant layer 14.

Second Embodiment

Figure 6:
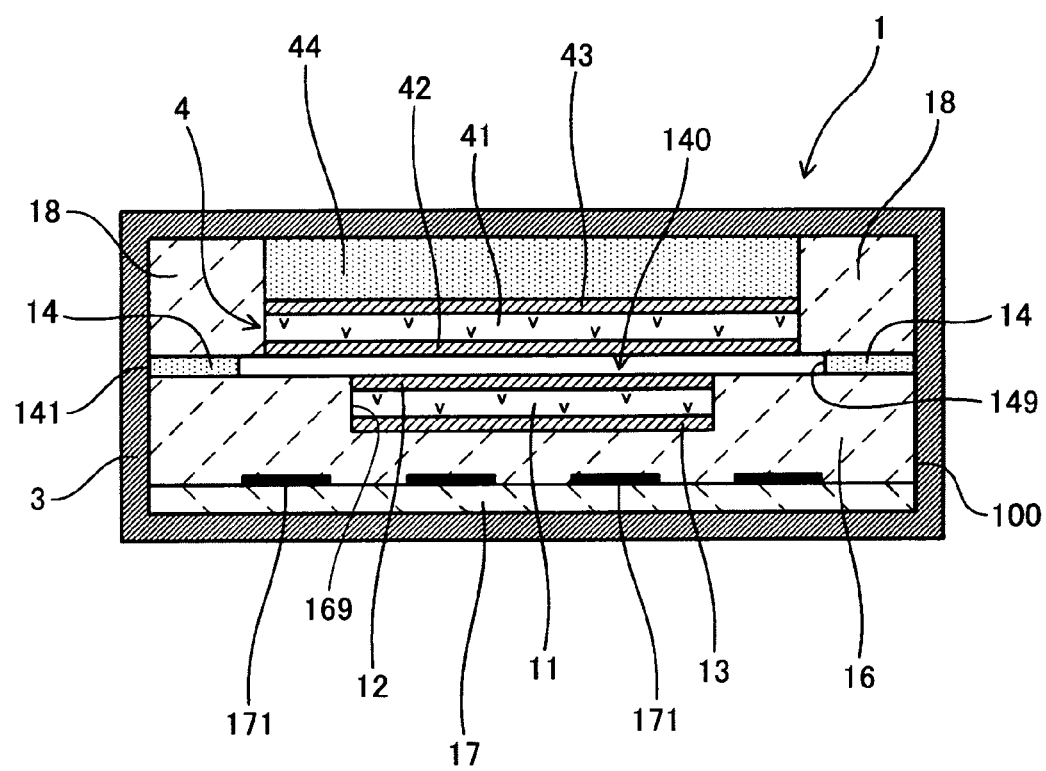
FIG. 6 is a cross-sectional view of a gas sensor element according to the second embodiment of the invention.

FIG. 6 shows the overall configuration of a gas sensor element 1 according to the second embodiment of the invention.

As shown in FIG. 6, in the present embodiment, the gas sensor element 1 further includes a pump cell 4 in addition to the solid electrolyte body 11, the measurement electrode 12, the reference electrode 13, and the porous diffusion-resistant layer 14.

It should be noted that the reference gas chamber 160 is not shown in FIG. 6. In addition, in the present embodiment, the solid electrolyte body 11 and the measurement and reference electrodes 12 and 13 are provided in the recess 169 of the reference gas chamber formation layer 16; the porous diffusion-resistant layer 14 is provided on the surface of the reference gas chamber formation layer 16 opposite to the heater substrate 17.

The pump cell 4 is provided to adjust the concentration of oxygen in the measurement gas chamber 140. The pump cell 4 is comprised of a solid electrolyte body 41 having oxygen ion conductivity and a pair of electrodes 42 and 43. The electrode 42 is provided on one surface (i.e., the lower surface in FIG. 6) of the solid electrolyte body 41 to face the measurement gas chamber 140, while the electrode 43 is provided on the other surface (i.e., the upper surface in FIG. 6) of the same to face a reference gas chamber (not shown in FIG. 6) of the pump cell 4. During operation of the gas sensor element 1, the reference gas chamber of the pump cell 4 will also be filled with the reference gas (i.e., air in the present embodiment).

Moreover, the gas sensor element 1 further includes a porous diffusion-resistant layer 44 provided on the electrode 43 of the pump cell 4 and a spacer layer 18 that is provided on the porous diffusion-resistant layer 14 around both the pump cell 4 and the porous diffusion-resistant layer 44.

In the present embodiment, the protective layer 3 is formed over the entire outer periphery 100 of the gas sensor element 1.

The gas sensor element 1 according to the present embodiment has the same advantages as the one according to the first embodiment.

[Modification 3]

Figure 7:
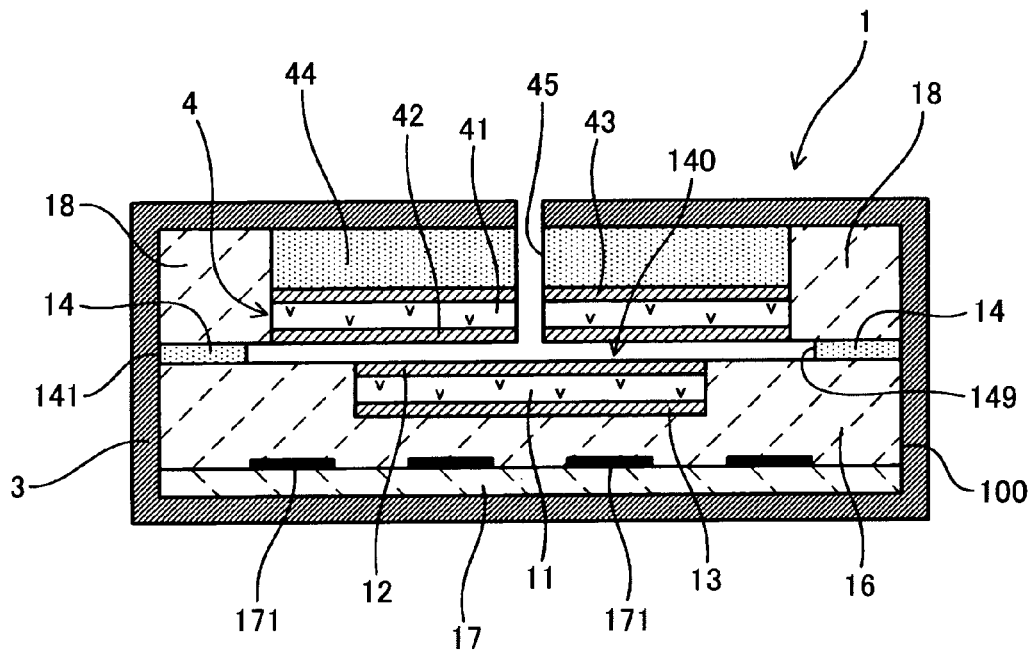
FIG. 7 is a cross-sectional view of a gas sensor element according to a modification of the second embodiment.

In this modification of the second embodiment, as shown in FIG. 7, there is further provided a communication hole 45 formed through the pump cell 4. The communication hole 45 extends between the outer periphery 100 of the gas sensor element 1 and the measurement gas chamber 140 so as to introduce the measurement gas into the measurement gas chamber 140.

Moreover, in this modification, the protective layer 3 is formed over the entire outer periphery 100 of the gas sensor element 1 except for the opening of the communication hole 45.

[Modification 4]

Figure 8:
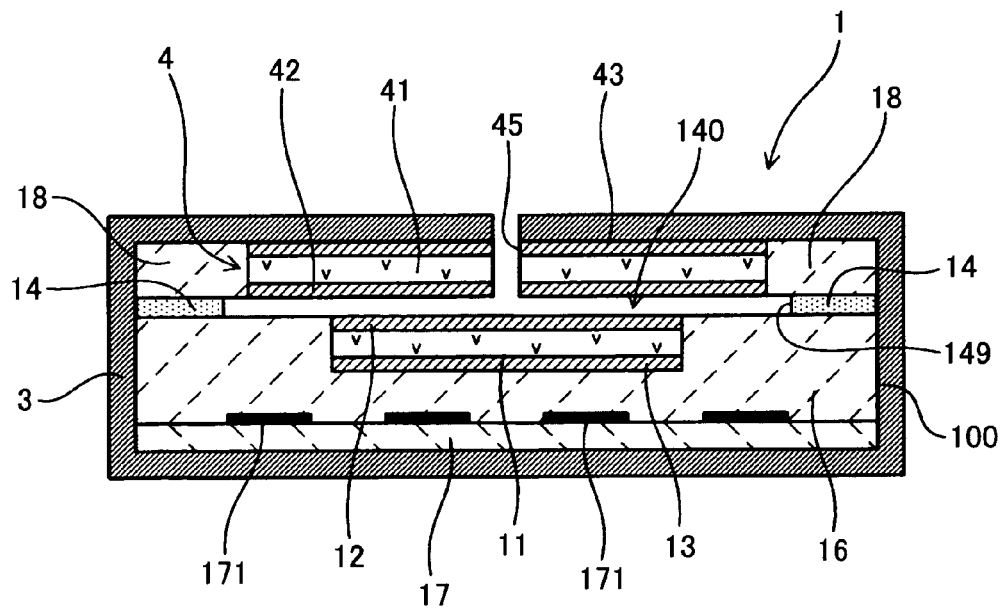
FIG. 8 is a cross-sectional view of a gas sensor element according to another modification of the second embodiment.

In this modification of the second embodiment, as shown in FIG. 8, there is also provided a communication hole 45 formed through the pump cell 4. The communication hole 45 extends between the outer periphery 100 of the gas sensor element 1 and the measurement gas chamber 140 so as to introduce the measurement gas into the measurement gas chamber 140. However, in this modification, the porous diffusion-resistant layer 44 is omitted from the gas sensor element 1.

Moreover, in this modification, the protective layer 3 is also fog used over the entire outer periphery 100 of the gas sensor element 1 except for the opening of the communication hole 45.

Third Embodiment

Figure 9:
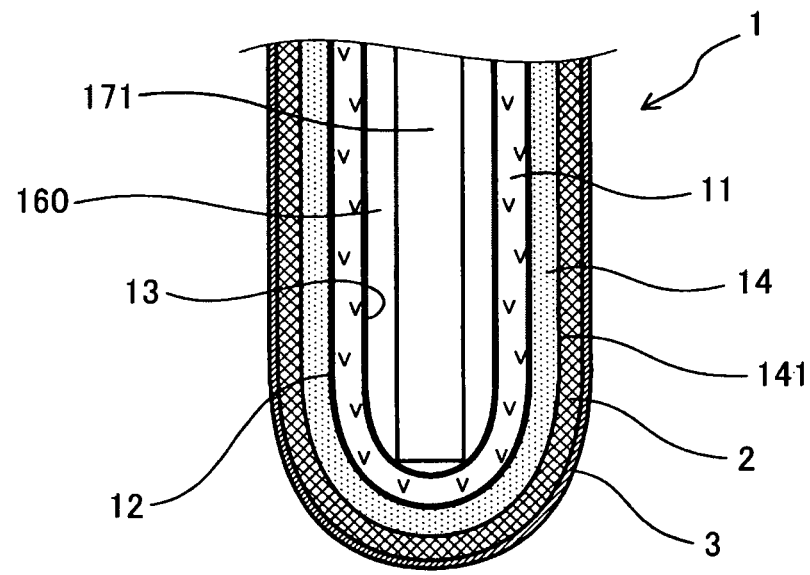
FIG. 9 is a cross-sectional view of a gas sensor element according to the third embodiment of the invention.

FIG. 9 shows the overall configuration of a gas sensor element 1 according to the third embodiment of the invention.

As shown in FIG. 9, in the present embodiment, the gas sensor element 1 is configured as a cup-type gas sensor element. In comparison, the gas sensor elements 1 according to the previous embodiments are of lamination type.

Specifically, in the present embodiment, the gas sensor element 1 includes a cup-shaped solid electrolyte body 11, a measurement electrode 12 provided on the outer surface of the solid electrolyte body 11, a reference electrode 13 provided on the inner surface of the solid electrolyte body 11, a porous diffusion-resistant layer 14, a trap layer 2, and a protective layer 3.

The solid electrolyte body 11 has oxygen ion conductivity and a reference gas chamber 160 formed therein. Within the reference gas chamber 160, there is disposed an electrical heating element 171.

The porous diffusion-resistant layer 14 is formed over the entire outer surface of the solid electrolyte body 11, covering the measurement electrode 12. During operation of the gas sensor element 1, a measurement gas will be introduced to the measurement electrode 12 through the porous diffusion-resistant layer 14.

The trap layer 2 and the protective layer 3 are formed in layers on the outer surface 141 of the porous diffusion-resistant layer 14, through which the measurement gas flows into the diffusion-resistant layer 14, so as to completely cover the outer surface 41. That is to say, in the present embodiment, the protective layer 3 is formed over the entire outer periphery of the gas sensor element 1.

The gas sensor element 1 according to the present embodiment also has the same advantages as the one according to the first embodiment.

[Modification 5]

Figure 10:
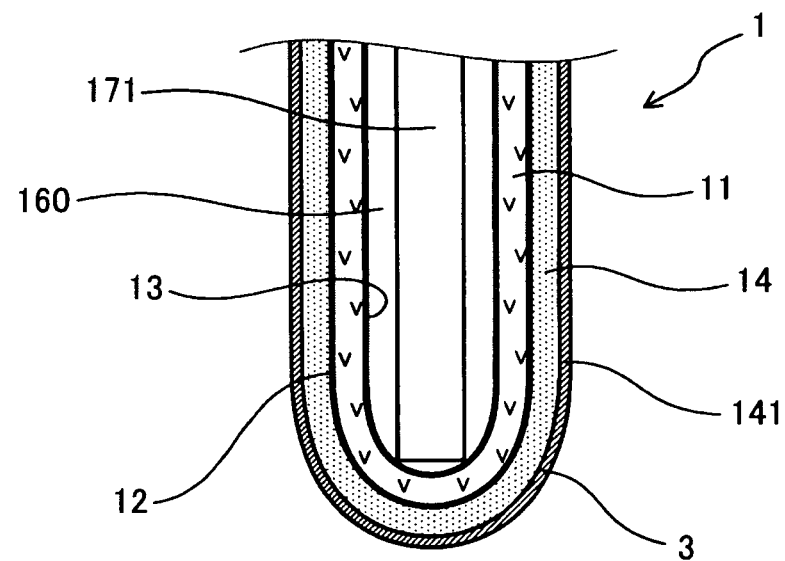
FIG. 10 is a cross-sectional view of a gas sensor element according to a modification of the third embodiment.

In this modification of the third embodiment, as shown in FIG. 10, the trap layer 2 is omitted from the gas sensor element 1, forming the protective layer 3 directly on the outer surface 141 of the porous diffusion-resistant layer 14.

[Experiment 1]

This experiment has been conducted to determine a preferable range of the surface roughness Ra of the protective layer in a gas sensor element according to the present invention.

In the experiment, a plurality of gas sensor element samples were prepared each of which had the same basic configuration as the gas sensor element 1 according to the first embodiment of the invention (see FIGS. 1 and 2). However, the surface roughness Ra of the protective layer was varied for those samples.

In the experiment, each of the samples was tested by the following steps.

In the first step, a given amount of water was dropped on the sample that had been previously heated to 700° C.

In the second step, it was checked whether water-induced cracking had occurred in the sample by conducting an A/F ratio inspection and a super-insulation inspection for the sample.

Specifically, the A/F ratio inspection was conducted by continuously monitoring the A/F ratio detected by the sample from when no water had been dropped on the sample. When the A/F ratio had increased by 5%, it was determined that water-induced cracking had occurred in the sample. Moreover, the super-insulation inspection was conducted by; (1) immersing the sample in a liquid mixture of (water:ethanol 4:1) for 1 minute; (2) applying a voltage of 500V across the measurement and reference electrodes of the sample; and (3) measuring the electrical resistance between the two electrodes. When the electrical resistance between the two electrodes of the sample had decreased below 10MΩ, it was determined that water-induced cracking had occurred in the sample.

In the third step, the sample was dried if water-induced cracking had not occurred yet.

The above steps were repeated by gradually increasing the amount of water to be dropped on the sample until water-induced cracking occurred in the sample. Then, the last amount of water was recorded as the necessary amount of water for causing cracking in the sample.

Figure 11:
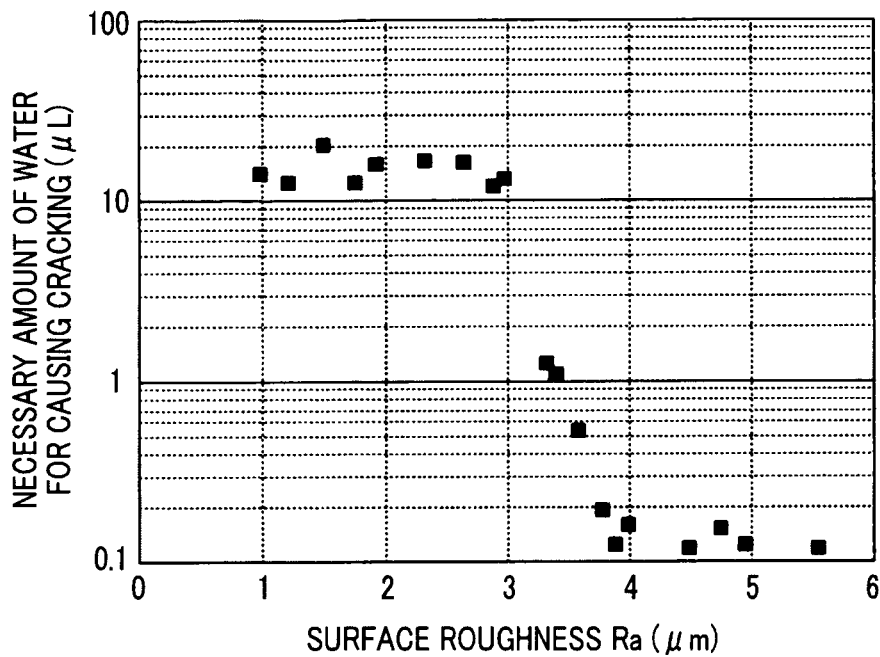
FIG. 11 is a graphical representation showing the results of Experiment 1 of the invention.

The test results for all the samples are shown in FIG. 11, where the horizontal axis indicates the surface roughness Ra of the protective layer (unit: μm), and the vertical axis indicates the necessary amount of water for causing cracking (unit: μL).

As can be seen from FIG. 11, when the surface roughness Ra of the protective layer was lower than or equal to 30 μm, the necessary amount of water for causing cracking was greater than 10 μL. However, with increase in the surface roughness Ra of the protective layer beyond 3.0 μm, the necessary amount of water for causing cracking rapidly decreased.

Accordingly, it is made clear from the above that to reliably prevent water-induced cracking from occurring in a gas sensor element, it is preferable to set the surface roughness Ra of the protective layer of the gas sensor element to be lower than or equal to 3.0 μm.

In addition, the surface roughness Ra of the protective layer has a correlation with the average particle diameter of the ceramic particles that form the protective layer. Therefore, in terms of suitably setting the average particle diameter to ensure high responsiveness of the gas sensor element, it is preferable to set the surface roughness Ra of the protective layer to be higher than or equal to 0.6 μm.

[Experiment 2]

This experiment has been conducted to determine a preferable range of the thickness of the protective layer in a gas sensor element according to the present invention.

In the experiment, a plurality of identical pairs of gas sensor element samples were prepared each of which had the same basic configuration as the gas sensor element 1 according to the first embodiment of the invention (see FIGS. 1 and 2). However, the thickness of the protective layer was varied for those pairs of the samples.

In the Experiment, each identical pair of the gas sensor element samples was tested by the following steps.

In the first step, a reference gas sensor and an evaluation gas sensor were prepared which respectively included the two identical samples of the pair.

In the second step, both the reference and evaluation gas sensors were mounted to an exhaust pipe of an internal combustion engine. Then, electric power was supplied to the heating elements of the reference gas sensor, thereby enabling the reference gas sensor to output the actual A/F ratio.

In the third step, the engine was started, and the A/F ratio of air-fuel mixture supplied to the engine was adjusted to render the A/F ratio output from the reference gas sensor equal to 16.

In the fourth step, electric power was also supplied to the heating elements of the evaluation gas sensor. Then, the length of time from when the supply of electric power to the heating elements of the evaluation gas sensor is started to when the A/F ratio output from the evaluation gas sensor becomes equal to 16 was measured as the activation time of the gas sensor sample included in the evaluation gas sensor.

Figure 12:
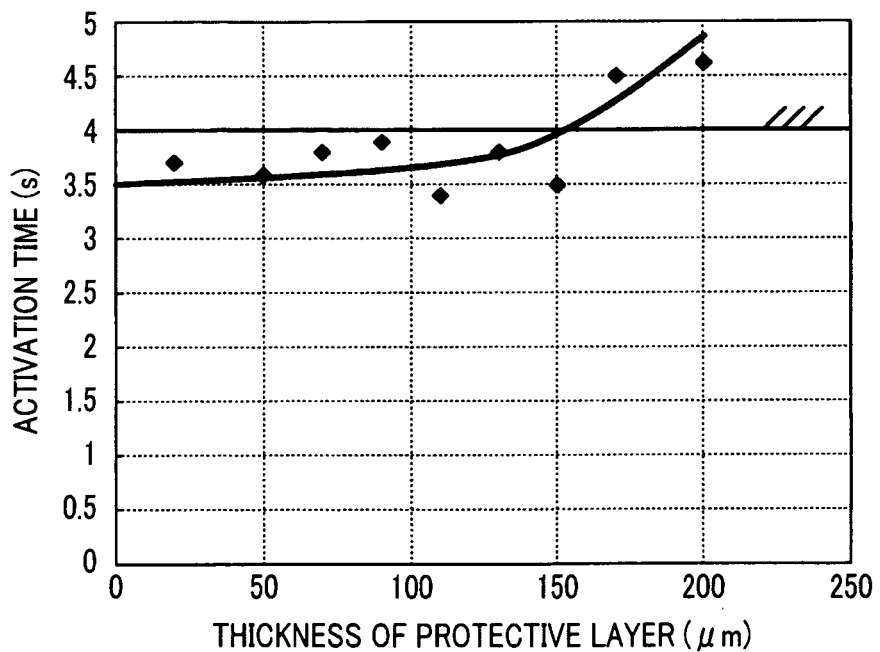
FIG. 12 is a graphical representation showing the results of Experiment 2 of the invention.

The test results for all the gas sensor samples are shown in FIG. 12, where the horizontal axis indicates the thickness of the protective layer (unit: μm), and the vertical axis indicates the activation time (unit: s).

As can be seen from FIG. 12, when the thickness of the protective layer was less than or equal to 150 μm, the activation time was shorter than 4 s. However, with increase in the thickness of the protective layer beyond 150 μm, the activation time rapidly increased to exceed 4 s.

Accordingly, it is made clear from the above that to ensure prompt activation of a gas sensor element, it is preferable to set the thickness of the protective layer to be less than or equal to 150 μm.

In addition, the thickness of the protective layer has a correlation with the surface roughness Ra of the protective layer. Therefore, in terms of reliably setting the surface roughness Ra to be lower than or equal to 3.0 μm, it is preferable to set the thickness of the protective layer to be greater than or equal to 20 μm.

[Experiment 3]

This experiment has been conducted to investigate the performance of gas sensor elements according to the present invention.

In the experiment, gas sensor element samples E1-E14 and C1-C4 were prepared each of which had the same basic configuration as the gas sensor element 1 according to the first embodiment of the invention (see FIGS. 1 and 2). All of the samples E1-E14 were made according to the present invention, but different from each other in at least one of the material of the protective layer, the surface roughness Ra of the protective layer, and the thickness of the protective layer. On the other hand, all of the samples C1-C4 were made not according to the present invention, but for comparison. The details of all the samples E1-E14 and C1-C4 are shown in FIG. 13.

In the experiment, each of the samples E1-E14 and C1-C4 were tested and evaluated in terms of capability of preventing water-induced cracking, activation time, responsiveness, and durability against poisoning substances as follows.

(1) For each of the samples, the necessary amount of water for causing, cracking in the sample was measured in the same manner as described in Experiment 1. Then, the sample was evaluated, in terms of capability of preventing water-induced cracking, as being preferable when the measured necessary amount of water was greater than or equal to 10 μL, and as being not preferable otherwise.

(2) For each of the samples, the activation time of the sample was measured in the same manner as described in Experiment 2. Then, the sample was evaluate as being preferable when the measured activation time was shorter than or equal to 4 s, and as being not preferable otherwise.

(3) For each of the samples, a response time of the sample was measured as follows.

First, the sample was mounted to an exhaust pipe of an internal combustion engine. Then, keeping the rotational speed of the engine at 2000 rpm and the temperature of the sample at about 730° C., the A/F ratio of the exhaust gas flowing through the exhaust pipe was alternately changed between 14 (i.e., rich) and 15 (i.e., lean); the delay of change in the output of the sample in following the alternate change in the A/F ratio was measured as the response time of the sample.

Thereafter, the sample was evaluated, in terms of responsiveness, as being preferable when the measured response time was shorter than or equal to 200 ms, and as being not preferable otherwise.

(4) For each of the samples, the responsiveness and LC (Limit Current) characteristics of the sample in a poisoning atmosphere were evaluated as follows.

First, the sample was mounted to an exhaust pipe of an internal combustion engine, and the engine was run on a gasoline fuel the silicon (Si) content of which was 0.5 cm³/L.

Then, keeping the rotational speed of the engine at 2000 rpm and the temperature of the sample at about 730° C., the A/F ratio of the exhaust gas flowing through the exhaust pipe was alternately changed between 13 (i.e., rich) and 18 (i.e., lean); the delay of change in the output of the sample in following the alternate change in the A/F ratio was measured as a response time of the sample.

Thereafter, the responsiveness of the sample was evaluated as being satisfactory when the measured response time was shorter than or equal to 300 ms, and as being not satisfactory otherwise.

Moreover, the limit currents of the sample at the A/F ratio of 13 and at the A/F ratio of 18 were measured. Then, the LC characteristics of the sample were evaluated as being satisfactory when the measured limit current at the A/F ratio of 13 was within (−0.26±0.067 mA) and the measured limit current at the A/F ratio of 18 was within (0.3±0.036 mA), and as being not satisfactory otherwise.

Furthermore, the sample was evaluated, in terms of durability against poisoning substances, as being preferable when both the responsiveness and LC characteristics were evaluated as being satisfactory, and as being not preferable otherwise.

The evaluation results for all the samples E1-E14 and C1-C4 are summarized in FIG. 13, where symbols "○" and "Δ" respectively denote "preferable" and "not preferable".

As can be seen from FIG. 13, each of the samples E1-E14 according to the present invention was evaluated as being preferable in terms of any of capability of preventing water-induced cracking, activation time, responsiveness, and durability against poisoning substances.

In comparison, the sample C1, in which the thickness of the protective layer was out of the preferable range of 20 to 150 μm, was evaluated as being not preferable in terms of both activation time and responsiveness. The sample C2, in which the surface roughness Ra of the protective layer was higher than 3.0 μm, was evaluated as being not preferable in terms of capability of preventing water-induced cracking. Moreover, each of the samples C3 and C4, in which the material of the protective layer was not hydrophilic (i.e., was hydrophobic), was evaluated as being not preferable in terms of activation time.

What is claimed is:

1. A gas sensor element comprising:
a solid electrolyte body having oxygen ion conductivity and an opposite pair of first and second surfaces; a measurement electrode provided on the first surface of the solid electrolyte body so as to be exposed to a measurement gas;
a reference electrode provided on the second surface of the solid electrolyte body so as to be exposed to a reference gas; and
a porous diffusion-resistant layer through which the measurement gas is introduced to the measurement electrode, the porous diffusion-resistant layer having an outer surface through which the measurement gas flows into the diffusion-resistant layer, characterized in that the gas sensor element further comprises a protective layer that is provided to cover at least the outer surface of the porous diffusion-resistant layer, the protective layer being hydrophilic at room temperature and water-repellent at high temperatures at which the solid electrolyte body can be activated; and wherein the protective layer has a surface roughness Ra lower than or equal to 3.0 μm;

wherein the protective layer is made of a ceramic comprising at least one of α-alumina, titania, zirconia, silicon carbide, silicon nitride, and zinc oxide; and further comprising a trap layer that is interposed between the outer surface of the porous diffusion-resistant layer and the protective layer to trap poisoning substances contained in the measurement gas.

2. The gas sensor element as set forth in claim 1, wherein the surface roughness Ra of the protective layer is higher than or equal to 0.6 μm.

3. The gas sensor element as set forth in claim 1, wherein the protective layer has a thickness in the range of 20 to 150 μm.

4. The gas sensor element as set forth in claim 1, wherein the protective layer is formed over an entire outer periphery of the gas sensor element.

5. The gas sensor element as set forth in claim 4, wherein a portion of the protective layer, which does not cover the outer surface of the porous diffusion-resistant layer, has a thickness less than or equal to 10 μm.

6. The gas sensor element as set forth in claim 5, wherein the thickness of the portion of the protective layer is greater than or equal to 5 μm.

7. The gas sensor element as set forth in claim 1, wherein the protective layer has a porosity in the range of 10 to 50%.

* * * * *